United States Patent [19]

Tanaka et al.

[11] 4,039,563
[45] Aug. 2, 1977

[54] PROCESS FOR PREPARING CYCLOPENT-2-EN-1-ONE DERIVATIVES

[75] Inventors: Toshio Tanaka; Seizi Kurozumi; Takeshi Toru; Shuji Miura; Makiko Kobayashi, all of Hino; Sachio Ishimoto, Tokyo, all of Japan

[73] Assignee: Teijin Limited, Osaka, Japan

[21] Appl. No.: 572,287

[22] Filed: Apr. 28, 1975

[30] Foreign Application Priority Data

May 2, 1974 Japan .................................. 49-48717

[51] Int. Cl.² .......................... C07C 49/46; C07B 3/00
[52] U.S. Cl. ............................ 260/410.9 R; 260/410; 260/413; 260/415; 260/448.8 R; 260/468 D; 260/514 D; 260/468 K; 260/514 K; 260/586 P; 260/586 R; 260/590 C; 260/696
[58] Field of Search ............... 260/586 P, 586 R, 410, 260/410.9 R, 413, 468 D, 514 D, 468 K, 514 K, 696

[56] References Cited

PUBLICATIONS

Attanasi, O. et al., "An Approach to the Prostaglandin Skeleton Through Organo-Borane Reactions,"-Gazzetta Chimica Italiana, 103(1973), pp 31-36.
Djerassi, C. et al., "Brominations with Pyridine Hydrobromide Perbromide," J. Am. Chem. Soc. 70 (1948) pp. 417-418.
Fieser & Fieser-Reagents for Organic Synthesis (1967), John Wiley & Sons, Inc., vol. I, pp. 967-970; vol. II, p. 350, vol. III, p. 131.
House, H. O., Modern Synthetic Reactions (2nd Ed-1972), W. A. Benjamin, Inc., Menlo Park, Calif. p. 427, pp. 465-467.

Primary Examiner—Helen M. McCarthy
Attorney, Agent, or Firm—Sherman & Shalloway

[57] ABSTRACT

A process for preparing cyclopent-2-en-1-one derivatives of the formula

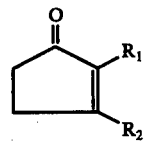

(I)

wherein
$R_1$ is a substituted or unsubstituted alkyl group or a substituted or unsubstituted aryl group, and
$R_2$ is a hydrogen atom or a substituent which is not substantially brominated under the treating conditions, which comprises treating a cyclopentanone derivative of the formula

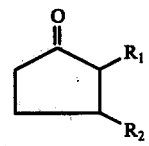

(II)

wherein
$R_1$ and $R_2$ are the same as defined above, with pyridinium hydrobromide perbromide.

13 Claims, No Drawings

PROCESS FOR PREPARING CYCLOPENT-2-EN-1-ONE DERIVATIVES

This invention relates to a novel process for preparing cyclopent-2-en-1-one derivatives, and more specifically, to a process for preparing cyclopent-2-en-1-one derivatives from cyclopentanone derivatives in one step.

Cyclopent-2-en-1-one derivatives are compounds of extreme commercial importance as raw materials for synthesizing such compounds as steroids, terpenoids, prostaglandins, jasmone, pyrethrin and analogs of these which are useful as medicines, agricultural chemicals or perfumes or intermediates for the synthesis of these. Some methods have previously been proposed for preparing these cyclopentenone derivitives.

Typical examples of these conventional methods include a method comprising enol-acetylating 2-(6-methoxycarbonylhexyl)-cyclopentan-1-one, brominating it with N-bromosuccinimide, and dehydrobrominating the product using lithium carbonate in pyridine thereby to form 2-(6-methoxycarbonylhexyl)-cyclopent-2-en-1-one (Journal of the American Chemical Society, 94, 7823, 1972); a method comprising enol-esterifying a 2-(ω-ethoxycarbonylalkyl)-cyclopentan-1-one, brominating the resulting ester, and then dehydrobrominating it to form a corresponding cyclopentenone derivative (Tetrahedron Letters, 4083, 1972); and a method comprising brominating a cyclopentanone derivative in tetrahydrofuran using phenyltrimethylammonium perbromide, and dehydrobrominating the resulting bromo-derivative with collidine to form a corresponding cyclopentenone derivative (Gazzetta Chimica Italiana 103, 31, 1973).

However, none of these conventional methods are fully satisfactory for commercial operations because all of them require two or more reaction steps, and the resulting yields are not so good. Commercially advantageous methods for preparing cyclopentenone derivatives have therefore been strongly desired.

It is an object of this invention to provide a process for preparing cyclopent-2-en-1-one derivatives, which are comercially very important as raw materials for the synthesis of medicines, agricultural chemicals, perfumes, and their intermediates, in a very simple manner and in a good yield.

We have now found unexpectedly that when pyridinium hydrobromide perbromide (PHP for short) frequently used as a brominating agent is caused to act on certain cyclopentanone derivatives, bromo-derivatives of the cyclopentanone derivatives are scarcely obtained, but the corresponding cyclopentenone derivatives having a double bond at the 2,3-positions can be obtained in high yields.

Thus, according to this invention, there is provided a process for preparing cyclopent-2-en-1 -one derivatives of the formula

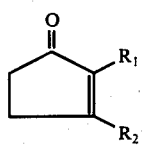

(I)

wherein $R_1$ is a substituted or unsubstituted alkyl group or a substituted or unsubstituted aryl group, and $R_2$ is a hydrogen atom or a substituent which is not substantially brominated under the treating conditions, which comprises treating cyclopentanone derivatives of the formula

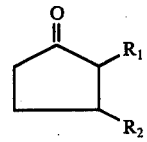

(II)

wherein $R_1$ and $R_2$ are the same as defined above, with pyridinium hydrobromide perbromide.

The "substituent which is not substantially brominated under the treating conditions" represented by $R_2$ may be any substituents which are not substantially brominated under the treating conditions employed in the present invention, and includes, for example, substituted or unsubstituted alkyl groups, substituted or unsubstituted aryl groups, a carboxyl group. Alkoxycarbonyl groups, aryloxycarbonyl groups, and a formyl group. The alkyl in the "substituted or unsubstituted alkyl group" may be a straight-chain, branched-chain or cyclic alkyl group containing up to 20 carbon atoms, preferably up to 10 carbon atoms, for example, methyl, ethyl, n- or isopropyl, n-, iso- or tert-butyl, pentyl, hexyl, heptyl, octyl, nonyl, decyl, cyclopentyl, and cyclohexyl. Examples of substituents for the alkyl group are a carboxyl group or carboxyl groups protected by a group capable of being split off by hydrolysis; alkoxy groups, especially those containing up to 10 carbon atoms, aryl groups, preferably phenyl, tolyl or xylyl; aryloxy groups, for example, phenoxy; aralkoxy groups, for example, benzyloxy; siloxy groups, for example, tert-butyldimethylsiloxy; dialkylamino groups, for example, dimethylamino; halogen atoms for example, fluorine, chlorine or bromine; and a hydroxyl group.

The aryl in the "substituted or unsubstituted aryl" is especially preferably phenyl. Examples of suitable substituents for the aryl are lower alkyl groups such as methyl or ethyl, lower alkoxy groups such as methoxy or ethoxy, halogen atoms such as fluorine or chloride, and lower haloalkyl groups such as trifluoromethyl.

Of the cyclopentanone derivatives of formula (II) used as the starting material in the process of this invention, those of the formula

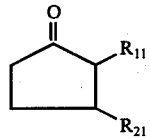

(III)

wherein $R_{11}$ is a substituted or unsubstituted alkyl group, and $R_{21}$ is a hydrogen atom or a substituted or unsubstituted alkyl group, are especially preferred. The substituted or unsubstituted alkyl groups represented by $R_{11}$ and $R_{21}$ in the above formula have the same meanings as described above.

Of the compounds of formula (III), cyclopentanone derivative of the formula

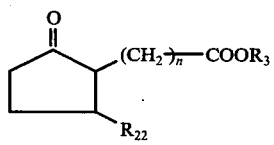

(IV)

wherein
$R_3$ is a hydrogen atom or a protective group capable of being split off by hydrolysis,
$R_{22}$ is a hydrogen atom or an alkyl group with up to 10 carbon atoms which may be substituted by an alkoxy or siloxy group, and $n$ is an integer of 1 to 8,
are especially preferred.

Especially preferred protective groups ($R_3$) in the above formula (IV) are alkyl groups, such as methyl, ethyl, n- or iso-propyl, n-, iso- or tert-butyl, pentyl, hexyl, cyclohexyl, octyl, decyl and dodecyl groups, especially those containing 1 to 4 carbon atoms, and aryl groups such as phenyl and p-nitrophenyl groups.

Suitable alkyl groups $R_{22}$ in the above formula (IV) are straight-chain, branched-chain or cyclic alkyl groups with up to 10 carbon atoms, especially up to 8 carbon atoms. The alkoxy as a substituent for the alkyl groups may be alkoxy groups with up to 10 carbon atoms, especially up to 6 carbon atoms, such as methoxy, ethoxy, n- or iso-propoxy, and n-, iso- or tert-butoxy. A suitable siloxy group is tert-butyldimethylsiloxy. Hydrogen is especially suitable as $R_{22}$.

Examples of compounds of formula (III) are as follows:

2-methoxycarbonylmethylcyclopentanone,
2-(2-methoxycarbonylethyl)-cyclopentanone,
2-(3-methoxycarbonylpropyl)-cyclopentanone,
2-(4-methoxycarbonylbutyl)-cyclopentanone,
2-(5-methoxycarbonylpentyl)-cyclopentanone,
2-(6-hydroxycarbonylhexyl)-cyclopentanone,
2-(6-methoxycarbonylhexyl)-cyclopentanone,
2-(6-ethoxycarbonylhexyl)-cyclopentanone,
2-(6-propoxycarbonylhexyl)-cyclopentanone,
2-(6-butoxycarbonylhexyl)-cyclopentanone,
2-(7-methoxycarbonylheptyl)cyclopentanone,
2-(8-methoxycarbonyloctyl)-cyclopentanone,
2-(6-methoxycarbonylhexyl)-3-methylcyclopentanone,
2-(6-methoxycarbonylhexyl)-3-ethylcyclopentanone,
2-(6-methoxycarbonylhexyl)-3-propylcyclopentanone,
2-)6-methoxycarbonylhexyl)-3-butylcyclopentanone,
2-(6-methoxycarbonylhexyl)-3-pentylcyclopentanone,
2-(6-methoxycarbonylhexyl)-3-hexylcyclopentanone,
2-(6-methoxycarbonylhexyl)-3-heptylcyclopentanone,
2-(6-methoxycarbonylhexyl)-3-octylcyclopentanone, and
2-(6-methoxycarbonylhexyl)-3-(3-t-butyldimethylsiloxyoctyl)-cyclopentanone.

Treatment of the cyclopentanone derivative of formula (II), (III) or (IV) with PHP can be achieved by contacting both with each other in an inert organic solvent, preferably with stirring. Examples of inert organic solvents that can be used are ethers such as tetrahydrofuran or dioxane, halogenated hydrocarbons such as chloroform or carbon tetrachloride, and hydrocarbons such as n-hexane, cyclohexane, petroleum ether, benzene or toluene. When a saturated aliphatic monocarboxylic acid which is liquid under the reaction conditions or a mixture of it with the above organic solvent is used in the process of this invention, the yield of the cyclopentenone derivative of formula (I) increases remarkably, and therefore, such a compound has been found to be especially suitable as a solvent for use in the process of this invention.

Preferred saturated aliphatic monocarboxylic acids suitable for use in the process of this invention are those containing up to 10 carbon atoms, especially acetic acid and propionic acid. Acetic acid is especially preferred.

The amount of PHP can be varied over a wide range according to the type of the starting cyclopentanone derivative, the reaction temperature, the reaction time, etc. Generally, it is 0.5 to 30 mols, preferably 0.8 to 5 mols, more preferably 1.2 to 3 mols, per mol of the cyclopentanone derivative.

The preferred reaction temperature is generally from room temperature to 100° C., especially from 40° to 60° C. The reaction time depends upon the reaction temperature. If, for example, the reaction temperature is 50° C., reaction periods of 3 to 5 hours are sufficient. The feasible reaction pressure is normal atmospheric pressure.

The reaction in accordance with this invention, if desired, can be carried out in an atmosphere of an inert gas. The proceeding of the reaction can be known by tracing the disappearance of the starting cyclopentanone derivative by such means as gas-chromatography or thin-layer chromatography.

It has further been found that when the treatment in accordance with the process of this invention is carried out in the presence of an organic base, specially an organic amine, the yield of the cyclopentenone derivative of formula (I) further increases. Tertiary organic amines are especially preferred as the organic amines. Examples of such amines are collidine, triethylamine, pyridine, lutidine, picoline, dimethylaniline, triethylenediamine, 1,5-diazabicyclo[4.3.0]-5-nonene, and 1,5-diazabicyclo[5,4,0]-5-undecene. Of these, pyridine and its methylsubstituted derivatives are especially effective.

The amount of the organic amine to be used is not critical, but generally, it is up to 30 mols, preferably 0.5 to 20 mols, more preferably 2 to 10 mols, per mol of the starting cyclopentanone derivative.

Thus, according to the process of this invention, the above cyclopentenone derivatives can be obtained in good yields by a single-step reaction. In particular, when cyclopentanone derivatives of formula (IV) in which $R_3$ is a protective group are treated with PHP in an organic solvent containing a saturated aliphatic monocarboxylic acid, at least a part of the —COOr$_3$ group undergoes hydrolysis depending upon the reaction temperature and/or time, and this may result in the formation of cyclopentenone derivatives of formula (V)

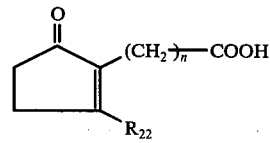

(V)

wherein
$R_{22}$ is the same as defined above, in which the protective group $R_3$ has been split off. Thus, the definition of the reaction product of formula (I) in the present specification and the appended claims should be understood as including such a hydrolyzed product.

The separation of the cyclopentenone derivative of formula (I) from the reaction mixture and its purification can be performed, for example, by a procedure which involves adding water to the resulting reaction mixture, neutralizing it with an aqueous solution of alkali such as sodium carbonate, extracting the product of formula (I) with an organic solvent, for example, an ether such as ethyl ether, a saturated hydrocarbon such as pentane, hexane or petroleum ether, an aromatic hydrocarbon such as benzene or toluene, or a halogenated hydrocarbon such as methylene chloride or chloroform, washing the resulting organic phase thoroughly with an aqueous solution of sodium carbonate, dilute hydrochloric acid, and aqueous solution of sodium chloride, etc., sufficiently drying the washed product with anhydrous sodium sulfate, concentrating it to form a crude product, and then purifying the crude product by distillation, column chromatography, or preparative thin-layer chromatography, etc. This results in the preparation of highly pure cyclopentenone derivatives of formula (I).

Where the starting material used in the process of this invention is a compound of formula (IV) in which $R_3$ is a protective group, a compound of formula (V) which may possibly be formed can be recovered by a procedure which comprises neutralizing the aqueous phase resulting after the separation of the organic phase with a dilute acid such as dilute hydrochloric acid until it assumes a weakly acidic pH, extracting the neutralized phase with ethyl acetate or ethyl ether in the same way as above, washing the resulting organic phase thoroughly with, for example, an aqueous solution of sodium chloride, then drying and concentrating it in the same way as above, and if desired, esterifying the concentrate in a customary manner, and then subjecting the product to the same purifying procedure as above, thereby to obtain the compound of formula (V) or its ester.

The process of this invention therefore provides, for example, the following compounds which are commercially important as raw materials for the synthesis of medicines, agricultural chemicals and perfumes with commercial advantage.

2-Methoxycarbonylmethylcyclopent-2-en-1-one,
2-(2-methoxycarbonylethyl)-cyclopent-2-en-1-one,
2-(3-methoxycarbonylpropyl)-cyclopent-2-en-1-one
2-(4-methoxycarbonylbutyl)-cyclopent-2-en-1-one,
2-(5-methoxycarbonylpentyl)-cyclopent-2-en-1-one,
2-(6-hydroxycarbonylhexyl)-cyclopent-2-en-1-one,
2-(6-methoxycarbonylhexyl)-cyclopent-2-en-1-one,
2-(6-ethoxycarbonylhexyl)-cyclopent-2-en-1-one,
2-(6-propoxycarbonylhexyl)-cyclopent-2-en1-one,
2-(6-butoxycarbonylhexyl)-cyclopent-2-en-1-one,
2-(7-methoxycarbonylheptyl)-cyclopent-2-en-1-one,
2-(8-methoxycarbonyloctyl)-cyclopent-2-en-1-one,
2-(6-methoxycarbonylhexyl)-3-methylcyclopent-2-en-1-one,
2-(6-methoxycarbonylhexyl)-3-ethylcyclopent-2-en-1-one,
2-(6-methoxycarbonylhexyl)-3-propylcyclopent-2-en-1-one,
2-(6-methoxycarbonylhexyl)-3-butylcyclopent-2-en-1-one,
2-(6-methoxycarbonylhexyl)-3-pentylcyclopent-2-en-1-one,
2-(6-methoxycarbonylhexyl)-3-hexylcyclopent-2-en-1-one,
2-(6-methoxycarbonylhexyl)-3-heptylcyclopent-2-en-1-one,
2-(6-methoxycarbonylhexyl)-3-octylcyclopent-2-en-1-one, and
2-)6-methoxycarbonylhexyl)-3-(3-t-butyldimethylsiloxyoctyl)-cyclopent-2-en-1-one.

The following Examples illustrate the present invention in greater detail.

EXAMPLE 1

Preparation of 2-(6-methoxycarbonylhexyl)-cyclopent-2-en-1-one a. 200 mg (0.88 mmol) of 2-(6-methoxycarbonylhexyl)-cyclopentanone was dissolved in 5 ml of acetic acid, and 0.5ml of pyridine and 560 mg (1.76 mmol) of pyridinium hydrobromide perbromide (PHP) were added to the solution, and the mixture was stirred at 60° C for 8 hours.

b. Acetic acid and pyridine were evaporated off from the reaction mixture at reduced pressure and a temperature below room temperature, and 1 ml. of methanol, 9 ml of dichloromethane and about 10 mg of p-toluenesulfonic acid were added to the resulting residue. An esterification was carried out with stirring at room temperature for 24 hours.

c. Methanol and dichloromethane were evaporated off at reduced pressure from this reaction mixture, and an aqueous solution of sodium carbonate was added to the residue, and it was extracted with ether. The ethereal phase separated was washed with an aqueous solution of sodium chloride, and then dried with anhydrous sodium sulfate. The dried product was concentrated at reduced pressure to afford 250 mg of a crude product.

d. The crude product was purified by preparative thin-layer chromatography using a 3:1 (volume) mixture of n-hexane and ethyl acetate as a developing solvent and silica gel (2 mm) as a carrier to afford 140 mg of a purified product.

e. The purified product exhibited the following spectra.

Infrared absorption (liquid film, cm$^{-1}$): 1720, 1690, 1620.

Nuclear magentic resonance absorption (CCl$_4$, $\delta$(ppm)):

7.20 (1H, an olefinic proton)
3.60 (3H, CH$_3$ of the ester)
2.70 - 1.10 (16H)

Mass analysis (m/e, 70 eV): 224 (M$^+$)

This product was identified as 2-(6-methoxycarbonylhexyl)-cyclopent-2-en-1-one from the above spectra. The yield was 71%.

The product showed a single peak in gas-chromatography (carrier: JXR silicone (Nippon Chromato Kabushiki Kaisha), 10%, 1 m × 3 mm$\phi$). This peak corresponded with the main peak seen in the gas-chromatogram of the reaction mixture before esterification, and thus it was confirmed that the above product was formed by the single-step reaction.

EXAMPLE 2

Preparation of
2-(6-methoxycarbonylhexyl)-cyclopent-2-en-1-one a. 4.52 g (20 mmol) of 2-(6-methoxycarbonylhexyl)-cyclopentanone was dissolved in 50 ml of acetic acid, and 5 ml of pyridine and 13 g (40 mmol) of PHP were added. The mixture was stirred at 60° C for 6 hours.

b. The reaction mixture was cooled, and about 100 ml of water was added. The mixture was neutralized with sodium carabonate, and extracted with ether to separate it into an ethereal phase and an aqueous phase.

c. The ethereal phase was washed thoroughly with an aqueous solution of sodium carbonate, dilute hydrochloric acid and an aqueous solution of sodium chloride, dried with anhydrous sodium sulfate, treated with activated carbon, and then concentrated to afford 5.72 g of a crude product.

The crude product was then purified by column chromatography using silica gel as a carrier, and from a fraction of a 2:1 mixture of benzene and ethyl acetate, 1.96 g (8.8 mol, yield 44%) of 2-(6-methoxycarbonylhexyl)-cyclopent-2-en-1-one having the same spectra as those of the purified product prepared in Example 1 was obtained.

From the benzene fraction, 280 mg (1.2 mmol; recovery rate 6%) of a compound corresponding with the starting 2-6-methoxycarbonylhexyl)-cyclopentanone was recovered.

d. On the other hand, the aqueous phase was acidified with dilute hydrochloric acid and extracted with ether. The ethereal phase separated was washed thoroughly with an aqueous solution of sodium chloride, and dried with anhydrous sodium sulfate. The dried product was concentrated, and 5 ml of methanol, 45 ml of dichloromethane and about 30 mg of p-toluenesulfonic acid were added to the resulting residue. An esterification reaction was carried out with stirring at room temperature for 24 hours.

The reaction mixture was treated in the same way as in (c) of Example 1, and the resulting crude product was subjected to column chromatography in the same way as above to afford 0.89 g (4 mmol, yield 20%) of 2-(6-methoxycarbonylhexyl)-cyclopent-2-en-1-one whose spectra corresponded with those of the purified product.

From the residue obtained in (c) and (d), it was ascertained that from 2-(6-methoxycarbonylhexyl)-cyclopentanone, the corresponding cyclopentenone derivative was obtained in a total yield of 64%.

EXAMPLE 3

Preparation of
2-(6-methoxycarbonylhexyl)-cyclopent-2-en-1-one a. 1.77 g (7.8 mmol) of 2-(6-methoxycarbonylhexyl)-cyclopentanone was dissolved in 50 ml of acetic acid, and 5.0 g (15.6 mmol) of PHP was added to the solution. The mixture was stirred at 40° C for 8 hours.

b. To the resulting reaction mixture was added about 100 ml of water, and the mixture was neutralized with sodium carbonate and then extracted with petroleum ether to separate it into a petroleum ether phase and an aqueous phase.

c. The petroleum ether phase was treated and purified by column chromatography in the same way as in Example 2, (c) to afford 175 mg (0.78 mmol; yield 10%) of 2-(6-methoxycarbonylhexyl)-cyclopent-2-en-1-one.

d. The aqueous phase was treated in the same way as in Example 2, (d) to afford 830 mg (3.7 mmol, yield 47%) of a methyl ester of the 2-(6-hydroxycarbonylhexyl)-cyclopent-2-en-1-one formed in the reaction mixture.

It was ascertained from the above results that the corresponding cyclopentenone derivative was obtained in a total yield of 57%.

EXAMPLE 4

Preparation of
2-(3-methoxycarbonylpropyl)-cyclopent-2-en-1-one a. 2.72 g (15 mmol) of 2-(3-methoxycarbonylpropyl)-cyclopentanone was dissolved in 50 ml of acetic acid, and 5 ml of pyridine and 9.6 g (30 mmol) of PHP were added to the solution. The mixture was stirred at 50° C for 5 hours.

b. The reaction mixture was treated in the same way as in Example 2, (b) to separate it into an ethereal phase and an aqueous phase.

c. The ethereal phase was washed thoroughly with an aqueous solution of sodium carbonate, dilute hydrochloric acid and then an aqueous solution of sodium chloride, dried with anhydrous sodium sulfate, and concentrated at reduced pressure to afford 2.19 g of a crude product.

The crude product was subject to column chromatography using silica gel as a carrier, and 770 mg (4.2 mmol, 28%) of a purified product was obtained from a 1:1 benzene-ethyl acetate fraction. The purified product showed the following spectra.

Infrared absorption (liquid film, cm$^{-1}$): 1730, 1700, 1630.

Nuclear magnetic resonance absorption ($CCl_4$, $\delta$(ppm)):

7.23 (1H, an olefinic proton)
3.60 (3H, $CH_3$ of the ester)
2.70 - 1.50 (10 H)

Mass analysis (m/e, 70 eV):
182 (M+).

This product was identified as 2-(3-methoxycarbonylpropyl)-cyclopent-2-en-1-one from the above spectra.

d. On the other hand, the aqueous phase was treated in the same way as in Example 2, (d), and 1.10 g (6.0 mmol) of a purified product having spectra corresponding with those of the 2-(3-methoxycarbonylpropyl)-cyclopent-2-en-1-one was obtained in a yield of 40%.

It was ascertained from the above results that the corresponding cyclopentenone derivative was obtained in a total yield of 68%.

EXAMPLE 5

Preparation of
2-(3-methoxycarbonylpropyl)-cyclopent-2-en-1-one a. 5.52 g (30 mmol) of 2-(3-methoxycarbonylpropyl)-cyclopentanone was dissolved in 50 ml of acetic acid, and 10 g (33 mmol) of PHP was added to the solution. The mixture was stirred at 50° C for 4 hours.

b. The reaction mixture was treated in the same way as in Example 4, (b), (c) and (d). From the ethereal phase, 350 mg (1.9 mmol) of 2-(3-methoxycarbonylpropyl)-cyclopent-2-en-1-one was obtained, and from the aqueous phase, 2.8 g (15.2 mmol) of the same compound was obtained. The total yield was 54%.

Furthermore, from the ethereal phase, 300 mg (1.6 mmols, recovery rate 5%) of the starting 2-(3-methoxycarbonylpropyl)-cyclopentanone was recovered.

EXAMPLE 6

Preparation of 2-(6-ethoxycarbonylhexyl)-3-methylcyclopent-2-en-1-one a. 200 mg (0.79 mmol) of 2-(6-methoxycarbonylhexyl)-cyclopentanone was dissolved in 10 ml of acetic acid, and 1 ml of pyridine and 500 mg (1.56 mmols) of PHP were added. The mixture was stirred at 60° C for 5 hours.

b. Acetic acid and pyridine were evaporated off at reduced pressure from the reaction mixture, and 1 ml of ethanol, 9 ml of dichlormethane and about 10 mg of p-toluenesulfonic acid were added to the resulting residue. An esterification reaction was carried out with stirring at room temperature for 24 hours.

c. The solvent was evaporated off from the reaction mixture, and an aqueous solution of sodium carbonate was added to the residue. The ethereal phase separated was washed thoroughly with an aqueous solution of sodium chloride, dried with anhydrous sodium carbonate, and then concentrated at reduced pressure to afford 220 mg of a crude product.

d. This crude product was treated and purified by preparative thin-layer chromatography in the same way as in Example 1, (d) to afford 70 mg of a purified product which showed the followed spectra.

Infrared absorption (liquid film, cm$^{-1}$):
1720, 1690, 1920.

Nuclear magnetic resonance absorption (CCl$_4$, $\delta$(ppm)):
1.29 (3H, CH$_3$ of the ethyl ester)
1.1–1.9 (8H, methylene groups)
2.1–2.7 (8H, methylene groups adjacent to a double bond or carbonyl groups)
2.05 (1H, a methine group at the 3-position of the cyclopentenone ring)
4.16 (2H, a methylene group of the ethyl ester)
Mass analysis (m/e, 70 eV):
252 (M+).

From the above spectra, this product was identified as 2-(6-ethoxycarbonylhexyl)-cyclopent-2-en-1-one. The yield was 35%.

COMPARATIVE EXAMPLE

Preparation of 2-(6-methoxycarbonylhexyl)-cyclopent-2-en-1-one using phenyltrimethylammonium perbromide instead of the pyridinium hydrobromide perbromide a. 100 mg (0.44 mmol) of 2-(6-methoxycarbonylhexyl)-cyclopentanone was dissolved in 1.5 ml of anhydrous tetrahydrofuran, and 226 mg (0.60 mmol) of phenyltrimethylammonium per bromide was added, and the mixture was stirred at room temperature for 1 hour.

b. Tetrahydrofuran was evaporated off from the reaction mixture at reduced pressure at a temperature below room temperature. A 5% aqueous solution of sodium carbonate was added to the resulting residue, and it was extracted with ether to separate it into an ethereal phase and an aqueous phase.

c. The ethereal phase was washed with an aqueous solution of sodium chloride and water, dried with anhydrous sodium sulfate, and concentrated at reduced pressure to afford 170 mg of a crude product. In the nuclear magnetic resonance absorption spectrum (60 MHz) of this product, the presence of an olefinic proton was not observed. Analysis of the product by thin-layer chromatography (carrier, silica gel; developing solvent, a 2:1 mixture of hexane and ethyl acetate) neither indicated any spot of 2-(6-methoxycarbonylhexyl)-cyclopent-2-en-1-one.

d. On the other hand, 0.5 ml of collidine was added to this crude product obtained from the ethereal phase. The mixture was reacted with stirring at 150° C for 5 minutes. After cooling, the mixture was extracted with ether. The ethereal phase collected was washed thoroughly with dilute hydrochloric acid and an aqueous solution of sodium chloride, dried with anhydrous sodium sulfate, and concentrated at reduced pressure to obtain 140 mg of the residue. The residue was purified by preparative thin-layer chromatography in the same way as in Example 1, (d) to afford 54 mg (0.24 mmol, yield 55%) of a purified product having spectra corresponding with those of 2-(6-methoxycarbonylhexyl)-cyclopent-2-en-1-one.

As is clear from the above results, when phenyltrimethylammonium perbromide, which is frequently used as a brominating agent similarly to the pyridinium hydrobromide perbromide used in this invention, is used, the corresponding cyclopentenone derivative cannot be obtained in a single step from the cyclopentanone derivative, but first, only the brominated cyclopentanone derivative is obtained. Subsequent dehydrobromination of this product gives the final product still in a lower yield than the present invention.

What we claim is:

1. A process for preparing cyclopent-2-en-1-one derivatives of the formula

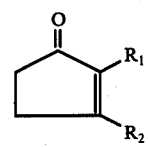

(I)

wherein R$_1$ is a substituted or unsubstituted alkyl group or a substituted or unsubstituted aryl group, and R$_2$ is a hydrogen atom or a substituent which is not substantially brominated under the treating conditions, which comprises treating, in a single step, a cyclopentanone derivative of the formula

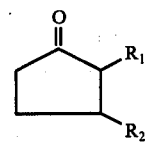

(II)

wherein R$_1$ and R$_2$ are the same as defined above, with pyridinium hydrobromide perbromide in an inert organic solvent selected from the group consisting of acetic acid and propionic acid wherein the derivative of formula (I) is formed as a result of said single-step treatment.

2. The process of claim 1 wherein said cyclopentanone derivative is a compound of the formula (III)

-continued

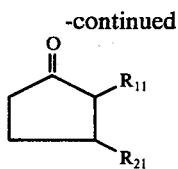

wherein $R_{11}$ is a substituted or unsubstituted alkyl group, and $R_{21}$ is a hydrogen atom or a substituted or unsubstituted alkyl group.

3. The process of claim 1 wherein said cyclopentanone derivative is a compound of the formula

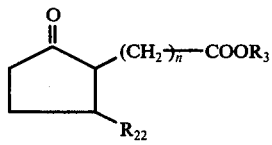 (IV)

wherein $R_3$ is a hydrogen atom or a proective group capable of being split off by hydrolysis, $R_{22}$ is a hydrogen atom or an alkyl group containing up to 10 carbon atoms which may be substituted by an alkoxy or siloxy group, and $n$ is an integer of 1 to 8.

4. The process of claim 1 wherein the treatment with the pyridinium hydrobromide perbromide is carried out in the presence of an organic amine.

5. The process of claim 4 wherein said organic amine is a tertiary organic amine.

6. The process of claim 1 wherein the amount of said pyridinium hydrobromide perbromide is 0.5 to 30 mols per mol of said cyclopentanone derivative.

7. The process of claim 1 wherein said treatment is carried out at room temperature to 100° C.

8. The process of claim 1 wherein a cyclopentanone derivative of the formula

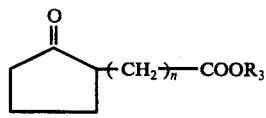

wherein
$R_3$ is a hydrogen atom or a protective group capable of being split off by hydrolysis, and $n$ is an integer of 1 to 8,
is contacted with pyridinium hydrobromide perbromide in a single step in acetic acid at room temperature to 100° C thereby to form a cyclopent-2-en-1-one derivative of the formula

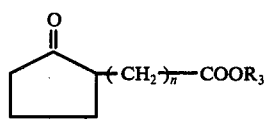

wherein
$R_3$ and $n$ are the same as defined above.

9. The process of claim 8 wherein the single step treatment with pyridinium hydrobromide perbromide is carried out in the presence of a tertiary organic amine.

10. The process according to claim 3 wherein $R_3$ is a hydrogen atom or a protective group selected from the group consisting of methyl, ethyl, n-propyl, iso-propyl, n-butyl, iso-butyl, tert-butyl, pentyl, hexyl, cyclohexyl, octyl, decyl, dodecyl, phenyl, and p-nitrophenyl; $R_{22}$ is a hydrogen atom or alkyl containing up to 8 carbon atoms which may be substituted by alkoxy of up to 6 carbon atoms or tert-butyldimethylsiloxy; the amount of pyridinium hydrobromide perbromide is 0.5 to 30 moles per mole of cyclopentanone derivative and the single step treatment is carried out at room temperature to 100° C.

11. The process of claim 10 wherein said cyclopentanone derivative is selected from the group consisting of:

2-methoxycarbonylmethylcyclopentanone,
2-(2-methoxycarbonylethyl)-cyclopentanone,
2-(3-methoxycarbonylpropyl)-cyclopentanone,
2-(4-methoxycarbonylbutyl)-cyclopentanone,
2-(5-methoxycarbonylpentyl)-cyclopentanone,
2-(6-hydroxycarbonylhexyl)-cyclopentanone,
2-(6-methoxycarbonylhexyl)-cyclopentanone,
2-(6-ethoxycarbonylhexyl)-cyclopentanone,
2-(6-propoxycarbonylhexyl)-cyclopentanone,
2-(6-butoxycarbonylhexyl)-cyclopentanone,
2-(7-methoxycarbonylheptyl)-cyclopentanone,
2-(8-methoxycarbonyloctyl)-cyclopentanone,
2-(6-methoxycarbonylhexyl)-3-methylcyclopentanone,
2-(6-methoxycarbonylhexyl)-3-ethylcyclopentanone,
2-(6-methoxycarbonylhexyl)-3-propylcyclopentanone,
2-(6-methoxycarbonylhexyl)-3-butylcyclopentanone,
2-(6-methoxycarbonylhexyl)-3-pentylcyclopentanone,
2-(6-methoxycarbonylhexyl)-3-hexylcyclopentanone,
2-(6-methoxycarbonylhexyl)-3-heptylcyclopentanone,
2-(6-methoxycarbonylhexyl)-3-octylcyclopentanone, and
2-(6-methoxycarbonylhexyl)-3-(3-t-butyldemethylsiloxyoctyl)-cyclopentanone;

the amount of said pyridinium hydrobromide perbromide is 0.8 to 5 moles per mole of cyclopentanone derivative; and said single step treatment is carried out at 40° to 50° C.

12. The process of claim 11 wherein said single step treatment is carried out in the presence of a tertiary organic amine selected from the group consisting of collidine, triethylamine, pyridine, lutidine, picoline, dimethylaniline, triethylenediamine, 1,5-diazabicyclo(4.3.0)-5-nonene, and 1,5-diazabicyclop(5.4.0)-5-undecene, wherein said amine is present in an amount from 0.5 to 20 moles per mole of the starting cyclopentanone derivative.

13. The process according to claim 12 wherein $R_{22}$ is a hydrogen atom, the inert organic solvent is acetic acid, the amount of the pyridinium hydrobromide perbromide is 1.2 to 3 moles per mole of cyclopentanone derivative, the tertiary amine is pyridine or its methyl-substituted derivative and the amount of said tertiary organic amine is from 2 to 10 moles, per mole of the starting cyclopentanone derivative.

* * * * *